(12) United States Patent
Kawagishi et al.

(10) Patent No.: US 8,540,636 B2
(45) Date of Patent: Sep. 24, 2013

(54) ULTRASONIC DIAGNOSTIC APPARATUS AND MEDICAL IMAGE PROCESSING APPARATUS

(75) Inventors: Tetsuya Kawagishi, Nasushiobara (JP); Susumu Uchiyama, Nasushiobara (JP); Shunsuke Satoh, Nasushiobara (JP); Shinichi Hashimoto, Otawara (JP); Yasuhiko Abe, Otawara (JP); Hiroyuki Ohuchi, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 424 days.

(21) Appl. No.: 13/019,669

(22) Filed: Feb. 2, 2011

(65) Prior Publication Data

US 2011/0190634 A1    Aug. 4, 2011

(30) Foreign Application Priority Data

Feb. 3, 2010  (JP) ................................. 2010-022506
Jan. 11, 2011  (JP) ................................. 2011-003228

(51) Int. Cl.
    *A61B 8/00*    (2006.01)
(52) U.S. Cl.
    USPC ............ 600/443; 600/437; 600/407; 382/128

(58) Field of Classification Search
    USPC .................. 600/443, 437, 450, 407; 382/128
    See application file for complete search history.

(56) References Cited

U.S. PATENT DOCUMENTS

| | | | |
|---|---|---|---|
| 7,803,113 B2 * | 9/2010 | Houle et al. .................. | 600/443 |
| 2007/0038087 A1 * | 2/2007 | Abe et al. ...................... | 600/437 |
| 2008/0267482 A1 * | 10/2008 | Abe et al. ...................... | 382/131 |
| 2010/0041992 A1 * | 2/2010 | Ohuchi et al. ................. | 600/443 |

* cited by examiner

*Primary Examiner* — Unsu Jung
*Assistant Examiner* — Rajeev Siripurapu
(74) *Attorney, Agent, or Firm* — Oblon, Spivak, McClelland, Maier & Neustadt, L.L.P.

(57) ABSTRACT

In general, according to one embodiment, an ultrasonic diagnostic apparatus includes an image generating unit configured to generate medical images from a multislice which covers an area including the heart of an object. Each slice is almost perpendicular to the long axis of the heart. Each medical image is a short-axis image of the heart. A series of medical images captured at different times correspond to each slice. The embodiment generates a polar map associated with myocardial motion indices from a plurality of medical images. A polar map is segmented into segments. The embodiment calculates the average value of motion indices for each segment. The utility of an average value depends on the range covered by each segment. This embodiment matches the boundary of a segment with the position of a vein. This prevents a deterioration in the utility of average values due to the influences of veins.

17 Claims, 11 Drawing Sheets

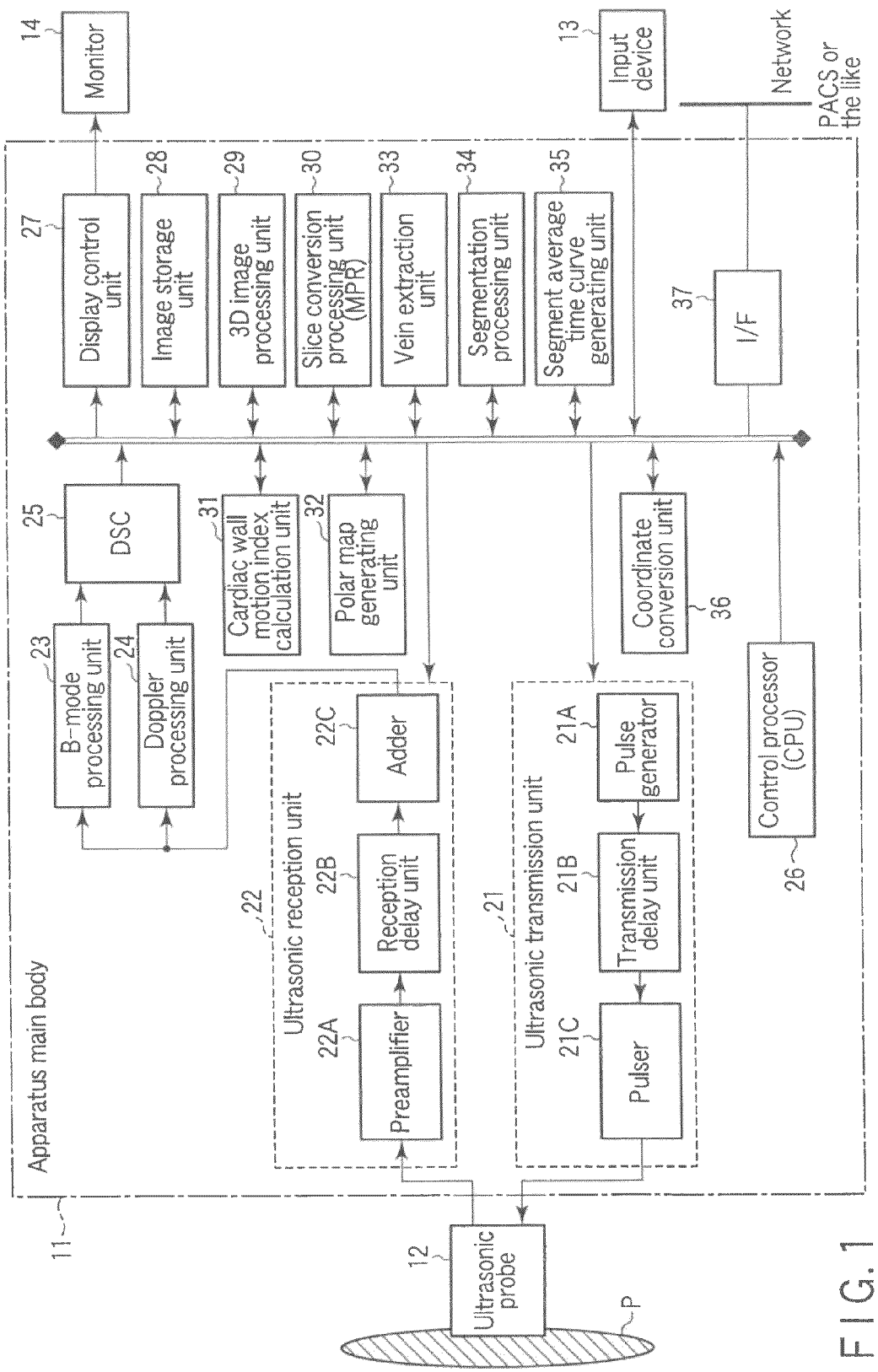
F I G. 1

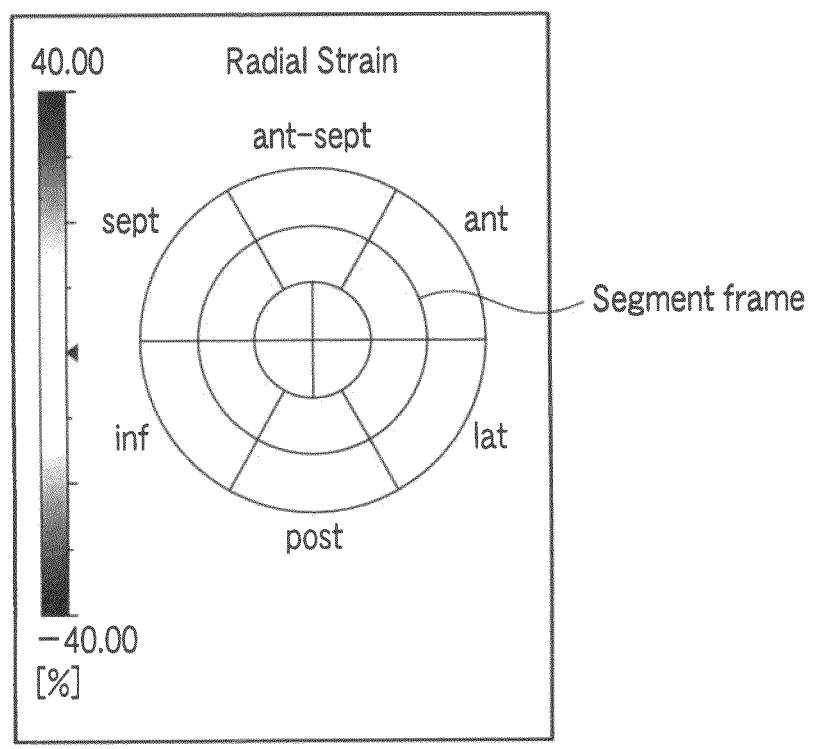
F I G. 7

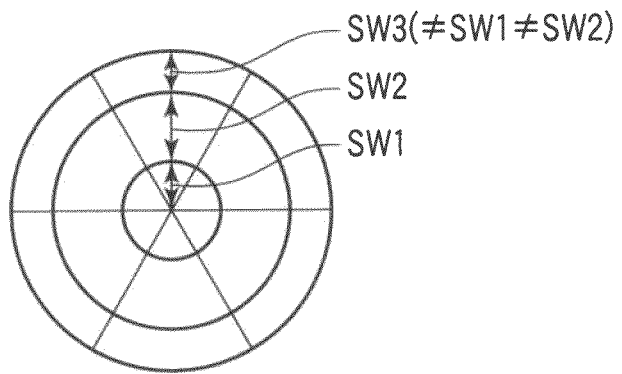
F I G. 14
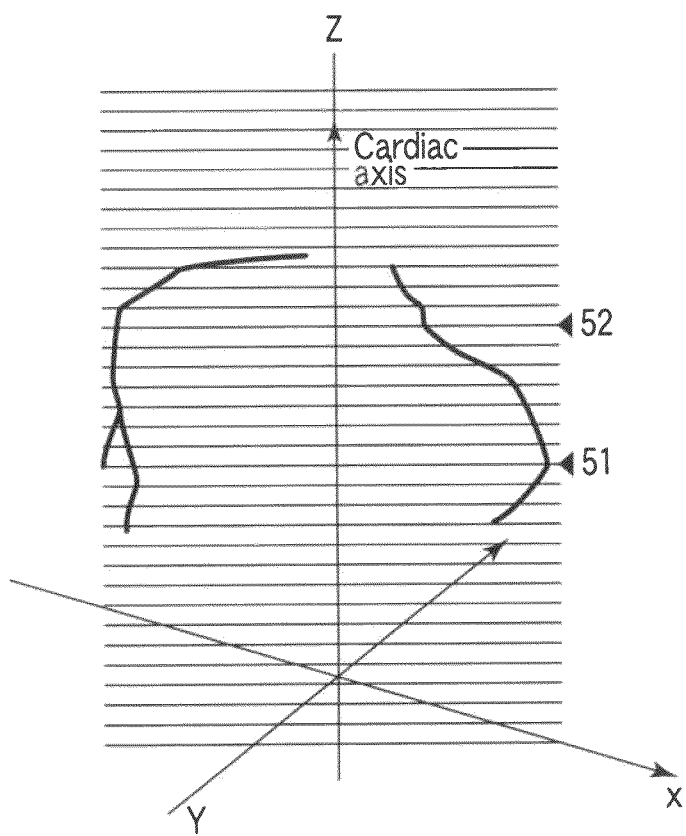
F I G. 15

US 8,540,636 B2

ULTRASONIC DIAGNOSTIC APPARATUS AND MEDICAL IMAGE PROCESSING APPARATUS

CROSS-REFERENCE TO RELATED APPLICATIONS

This application is based upon and claims the benefit of priority from Japanese Patent Applications No. 2010-022506, filed Feb. 3, 2010; and No. 2011-003228, filed Jan. 11, 2011; the entire contents of both of which are incorporated herein by reference.

FIELD

Embodiments described herein relate generally to an ultrasonic diagnostic apparatus and a medical image processing apparatus.

BACKGROUND

CRT is a treatment method for asynchronous cardiac motion. There is a need to set the position of the lead at a portion exhibiting asynchrony most noticeably. In this case, the positions of the great cardiac vein and anterior vein serve as landmarks.

The evaluation of asynchrony includes parametric imaging (a polar coordinate distribution, also called a polar map) based on wall motion tracking (cardiac wall tracking). This technique can identify a delayed region but does not provide a clear positional relationship with the above veins.

The above wall motion tracking allows to calculate a motor function index (motion index) of the cardiac wall, e.g., the change rate of cardiac wall thickness, for each minute section of a cardiac phase or in the interval between an end diastole (ED) and an end systole (ES), at multiple points throughout the heart. Note however that the heart is vertically long from the apex portion to the base portion. A polar coordinate distribution generally called a polar map is often generated as a display form of motion indices to allow to observe, at a glance, the motion indices of the overall heart which is vertically long. As is known, an expression method using polar coordinates is a method of expressing a plane by (r, θ) wherein θ represents an angle around the cardiac axis, and r represents a slice number assigned to each short-axis image of the region from the apex portion to the base portion.

This technique also segments a polar coordinate distribution into a plurality of segments in the radial and circumferential directions, calculates the average value of motion indices for each segment, and displays segment frames in color with hues corresponding to the average values. The technique also generates a temporal change in the average value of motion indices for each segment, and simultaneously displays the temporal changes. The polar coordinate distribution is segmented into segments uniformly in the circumferential direction regardless of the cardiac tissue. Average values vary depending on the range of cardiac tissue covered by each segment. For this reason, the reliability of temporal changes in the average value of motion indices are not very high.

For the above reasons, the utility value of a polar coordinate distribution associated with the motor function indices of the cardiac wall is not very high.

BRIEF DESCRIPTION OF THE DRAWINGS

FIG. 1 is a block diagram showing the arrangement of an ultrasonic diagnostic apparatus according to an embodiment;

FIG. 7 is a view showing a polar map generated by the polar map generating unit in FIG. 1;

FIG. 14 is a view showing a segment set whose width is adjusted by the segmentation processing unit in FIG. 1 in accordance with the bending position of a vein on a long-axis plane;

FIG. 15 is a view showing the run of veins on a long-axis image for supplementation of FIG. 14;

DETAILED DESCRIPTION

Figure 2:
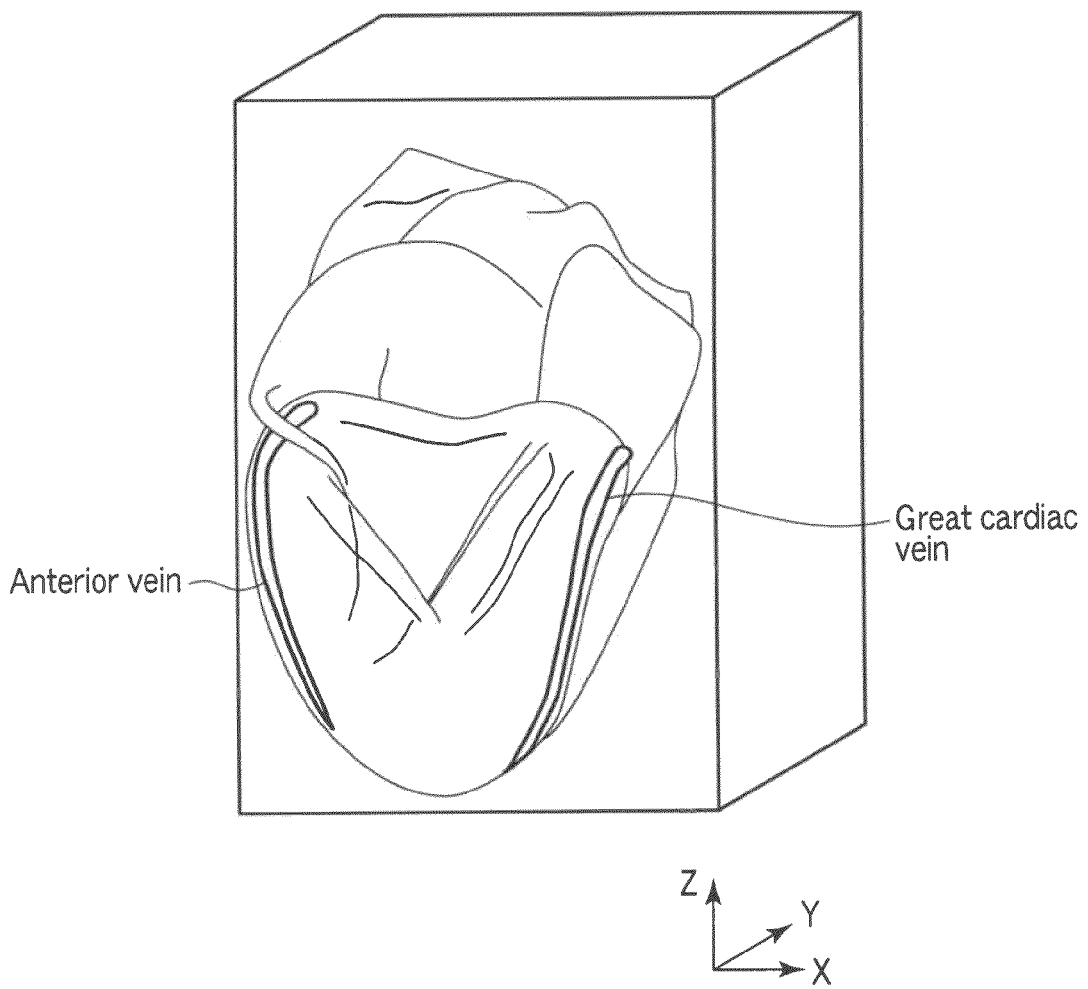
FIG. 2 is a view showing three-dimensional ultrasonic image data stored in an image storage unit in FIG. 1.

In general, according to one embodiment, an ultrasonic diagnostic apparatus includes an image generating unit configured to generate a plurality of medical images from a multislice which covers an area including the heart of an object. Each slice is almost perpendicular to the long axis of the heart. Each medical image is a short-axis image of the heart. A series of medical images captured at different times correspond to each slice. The embodiment generates a polar map associated with myocardial motion indices from a plurality of medical images. A polar map is segmented into a plurality of segments. The embodiment calculates the average value of motion indices for each segment. The utility of an average value depends on the range covered by each segment. This embodiment matches the boundary of a segment with the position of a vein. This prevents a deterioration in the utility of average values due to the influences of veins.

Medical images to be processed by this embodiment are based on a condition that they are generated by an imaging technique capable of forming a multislice and a series of medical images. The most typical images are three-dimensional ultrasonic images generated by an ultrasonic diagnostic apparatus. However, this embodiment can process CT images obtained by an X-ray computed tomography apparatus, MR images obtained by a magnetic resonance imaging apparatus (MRI), gamma images obtained by a nuclear medicine diagnostic apparatus, and X-ray images obtained by an X-ray diagnostic apparatus which can perform stereoscopic imaging by vibrating a C-arm. The following will exemplify three-dimensional ultrasonic images generated by a typical ultrasonic diagnostic apparatus.

In addition, this embodiment may be provided by mounting a corresponding image processing unit in an image capturing apparatus such as an ultrasonic diagnostic apparatus or may be provided as a medical image processing apparatus independently of an image capturing apparatus.

FIG. 1 shows the arrangement of an ultrasonic diagnostic apparatus according to this embodiment. This ultrasonic diagnostic apparatus includes an ultrasonic diagnostic apparatus main body 11, an ultrasonic probe 12, an input device 13, and a monitor 14. The ultrasonic probe 12 generates ultrasonic waves based on driving signals supplied from the ultrasonic transmission unit 21 of the apparatus main body 11. The ultrasonic probe 12 also converts reflected waves from an object into electrical signals. For this purpose, the ultrasonic probe 12 includes a plurality of piezoelectric transducers. The ultrasonic probe 12 has an acoustic matching layer provided on the front side of the piezoelectric transducers, and a backing member on the rear side of the piezoelectric transducers. The plurality of piezoelectric transducers are arranged in a two-dimensional array to electrically perform three-dimensional scanning.

The ultrasonic waves transmitted from the ultrasonic probe 12 to an object P are sequentially reflected by an acoustic-impedance discontinuity surface in an internal body tissue. The ultrasonic probe 12 receives the echo signal. The amplitude of this echo signal depends on an acoustic impedance difference on the discontinuity surface by which the echo signal is reflected. When the transmitted ultrasonic waves are reflected by the surface of a moving object such as a moving blood flow or a cardiac wall, the echo signal is subjected to a frequency shift depending on the velocity component of the moving object in the ultrasonic transmission direction due to a Doppler effect.

An ultrasonic transmission unit 21 includes a pulse generator 21A, a transmission delay unit 21B, and pulser 21C. The pulse generator 21A repetitively generates rate pulses for the formation of transmission ultrasonic waves at a predetermined rate frequency fr Hz (period: 1/fr sec). The transmission delay unit 21B gives each rate pulse for each channel a delay time necessary to focus an ultrasonic wave into a beam and determine transmission directivity for each channel. The pulse generator 21A applies a driving pulse to the ultrasonic probe 12 for each channel at the timing based on this rate pulse.

An ultrasonic reception unit 22 includes a preamplifier 22A, an A/D converter (not shown), a reception delay unit 22B, and an adder 22C. The preamplifier 22A amplifies an echo signal captured via the probe 12 for each channel. The reception delay unit 22B gives the amplified echo signals delay times necessary to determine reception directivities. The adder 22C then performs addition processing for the signals. With this addition, the reflection component of the echo signal from the direction corresponding to the reception directivity is enhanced, and a composite beam for ultrasonic transmission/reception is formed in accordance with the reception directivity and transmission directivity.

The input device 13 is connected to an apparatus main body 11 and includes various types of switches, buttons, a trackball, a mouse, and a keyboard which are used to input, to the apparatus main body 11, various types of instructions, conditions, an instruction to set a region of interest (ROI), various types of image quality condition setting instructions, and the like from an operator. The monitor 14 displays morphological information and blood flow information in the living body as images based on video signals from a display control unit 27.

The apparatus main body 11 includes a control processor 26 which controls the overall operation of the apparatus, a B-mode processing unit 23, and a Doppler processing unit 24, in addition to the ultrasonic transmission unit 21 and the ultrasonic reception unit 22.

The B-mode processing unit 23 generates the data of a B-mode image from an echo signal from the ultrasonic reception unit 22 by performing logarithmic amplification, envelope detection processing, and the like for the signal. The display control unit 27 converts the B-mode image data into display data whose reflected wave intensity is expressed by display luminance by using a lookup table.

The Doppler processing unit 24 extracts a shift frequency generated by the Doppler effect of the echo signal received from the ultrasonic reception unit 22, and mainly extracts a blood flow component as a moving object, thus obtaining blood flow data such as an average velocity, variance, and power at each of multiple points. The obtained blood flow data is sent to a digital scan converter (DSC) 25 to be converted into an average velocity image, variance image, power image, and a combined image of them. Note that B-mode image data, average velocity image data based on the Doppler effect, and the like will be generically referred to as ultrasonic image data.

The digital scan converter 25 converts the scanning line signal string for ultrasonic scanning into a scanning line signal string in a general video format typified by a TV format. An image storage unit 28 stores the converted ultrasonic image data.

An interface unit 37 is connected to an external image storage device (not shown) such as a PACS via a network. The external image storage device stores the medical image data generated by medical image capturing apparatuses such as an X-ray computed tomography apparatus and a magnetic resonance imaging apparatus.

This embodiment has a function of calculating indices (cardiac wall motion indices) associated with the motor function of the cardiac wall from a multislice or volume throughout a plurality of cardiac phases which is obtained by repeatedly three-dimensionally scanning a specific organ of an object (in this case, a three-dimensional area including the cardiac region exemplified in FIG. 2) with ultrasonic waves, and generating a so-called polar map by distributing the calculated cardiac wall motion indices in a polar coordinate system.

Figure 3:
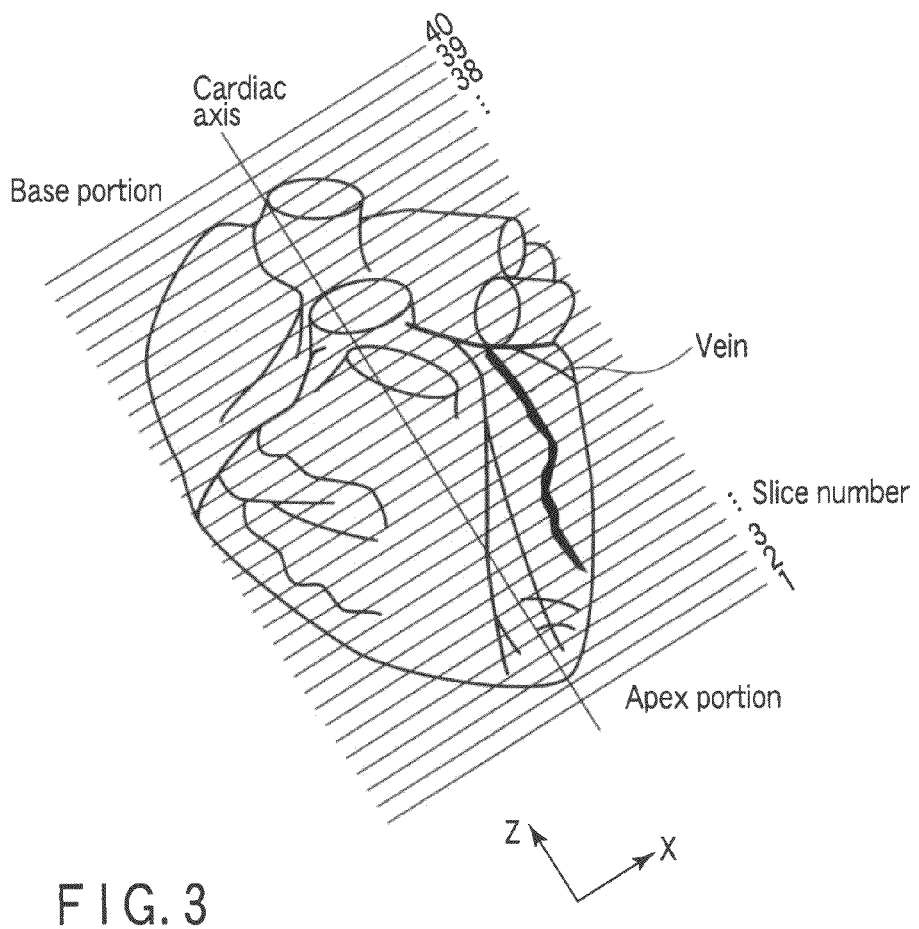
FIG. 3 is a view showing a short-axis image slice generated by a slice conversion unit in FIG. 1.
Figure 4:
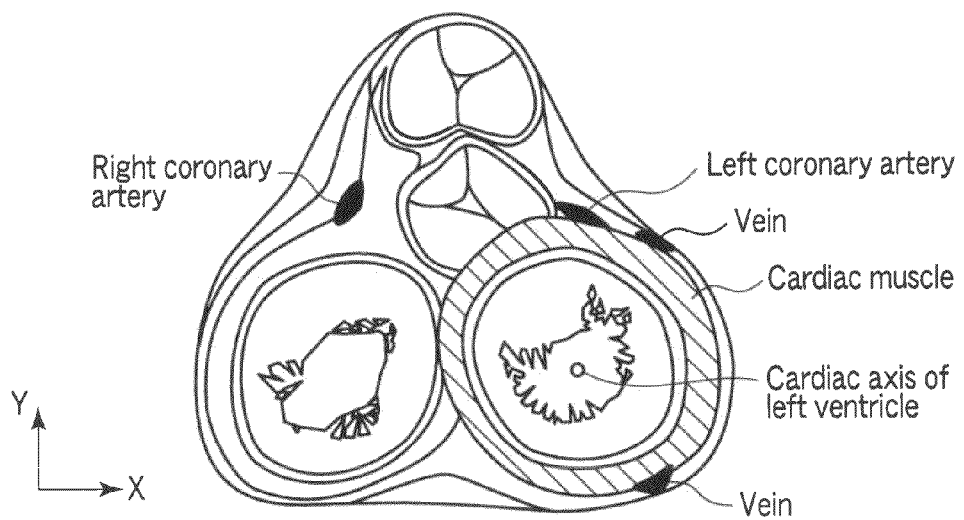
FIG. 4 is a view showing the tissue structure of the slice in FIG. 3.

As shown in FIG. 3, a slice conversion processing unit (MPR) 30 extracts the cardiac axis of the left ventricle automatically recognized from three-dimensional ultrasonic image data at a given cardiac phase and generates a plurality of tomograms (short-axis images) respectively corresponding to a plurality of slices perpendicular to the cardiac axis. In the same manner, the slice conversion processing unit 30 generates short-axis images respectively corresponding to each slice at all cardiac phases. For reference, FIG. 4 shows the tissue structure of a short-axis image.

Figure 5:
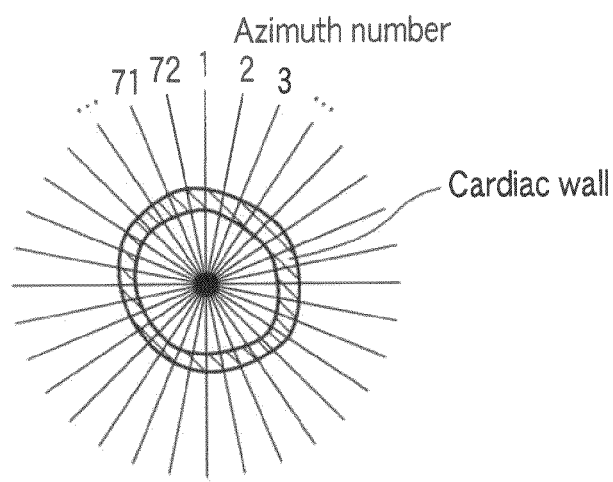
FIG. 5 is a view for supplementarily explaining index calculation by a cardiac wall motion index calculation unit in FIG. 1.

A cardiac wall motion index calculation unit 31 calculates a cardiac wall motion index associated with a change in cardiac wall thickness between short-axis images at different cardiac phases, for example, adjacent short-axis images on the time axis, for each slice, in each of a plurality of directions radially extending from the cardiac axis as the center, as shown in FIG. 5. Cardiac wall motion indices include the following types, an arbitrary type of which is selected via the input device 13:

a change in the thickness difference between the cardiac wall thickness of the left ventricle at a given cardiac phase and the cardiac wall thickness of the left ventricle at another cardiac phase or a volume/radius change (Wall Motion) obtained from the thickness difference;

the left ventricle myocardial wall thickness change rate (Wall Thickening) obtained by dividing (normalizing) the difference between the cardiac wall thickness of the left ventricle at a given cardiac phase and the cardiac wall thickness of the left ventricle at another cardiac phase by another left ventricle cardiac wall thickness; and the volume change rate (Regional EF) obtained by dividing the volume change obtained by subtracting, from the square of the left ventricle myocardial inside diameter at a given cardiac phase, the square of the left ventricle myocardial inside diameter at another cardiac phase, by the square of the left ventricle myocardial inside diameter at another cardiac phase.

Figure 6:
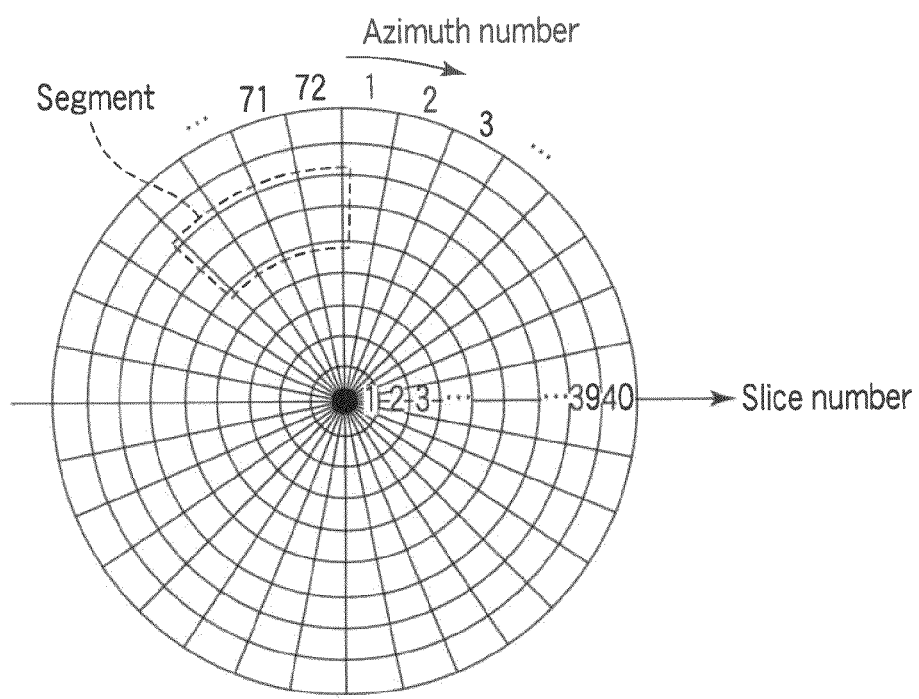
FIG. 6 is a view showing polar coordinates generated by a polar map generating unit in FIG. 1.

A polar map generating unit 32 generates the polar map exemplified in FIG. 7 by plotting the cardiac wall motion indices calculated by the cardiac wall motion index calculation unit 31 at positions corresponding to the directions of concentric circles corresponding to the slice numbers, on a polar map template of a polar coordinate system centered on the cardiac axis, as shown FIG. 6.

A vein extraction unit 33 extracts the vein areas shown in FIGS. 2, 3, and 4 from each of a plurality of short-axis images at an end diastole generated by the slice conversion processing unit 30. Note that the vein extraction unit 33 may extract a vein area by the positions designated on a plurality of short-axis images by the operator via the input device 13. The vein extraction unit 33 also extracts vein areas from a long-axis image passing through the cardiac axis generated by the slice conversion processing unit 30. Note that the vein extraction unit 33 may extract a vein area by connecting a plurality of positions designated on a long-axis image by the operator via the input device 13. Typically, pattern matching processing using a vein pattern is applied to these types of vein area extraction processing.

Figure 17:
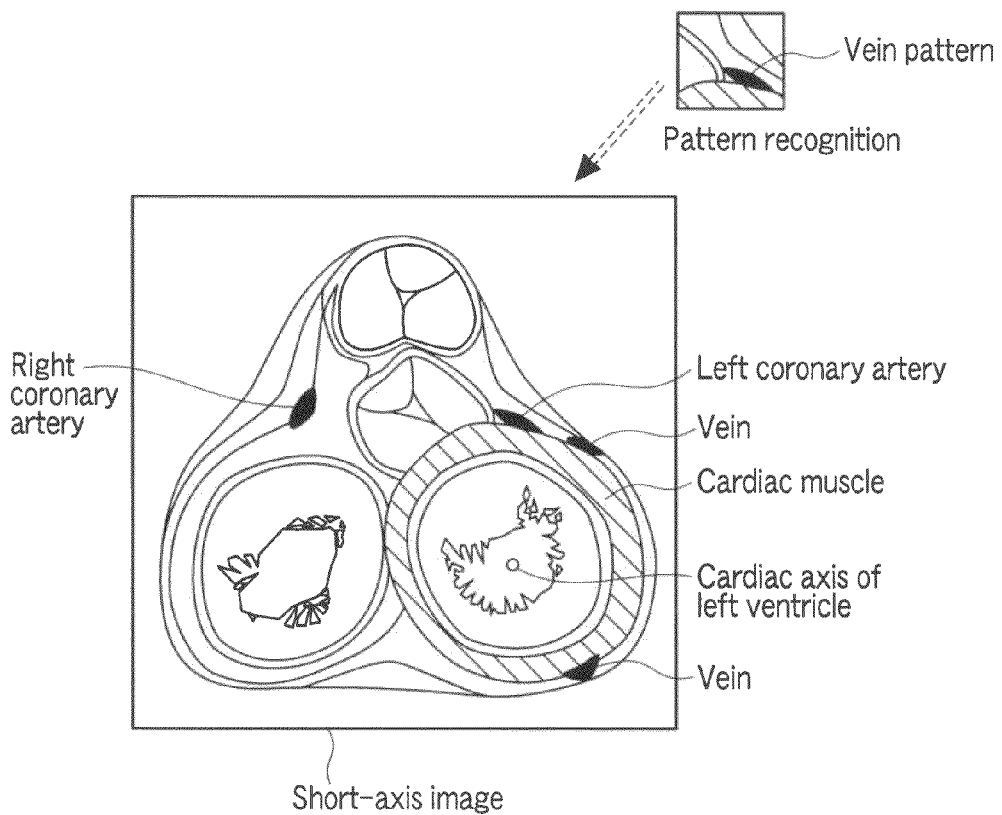
FIG. 17 is a view for explaining a vein extraction method executed by a vein extraction unit in FIG. 1.

The vein extraction unit 33 extracts one or two vein positions around the cardiac wall of the left ventricle on a short-axis image by, for example, a pattern matching technique. As shown in FIG. 17, a plurality of kinds of vein patterns are prepared in advance based on a plurality of short-axis cardiac images originating from able-bodied persons and disable-bodied persons. The operator selects an arbitrary kind of vein pattern. A vein pattern is a local image of a local area centered on a vein or a modified image of the local image. In pattern matching, a reference pattern is moved relative to a short-axis image of the object. This apparatus then calculates the correlation coefficient between the reference pattern and a local portion of a short-axis image of the object at each position. The apparatus specifies a position exhibiting the highest correlation coefficient. The apparatus identifies, as a vein position, the central position of the reference pattern at the specified position.

The type of image to which vein area extraction processing is to be applied is not limited to ultrasonic images. It is possible to acquire tomograms or volume data acquired from the same object by X-ray CT or MRI or standard human model data from a PACS or the like via a network.

Figure 9:
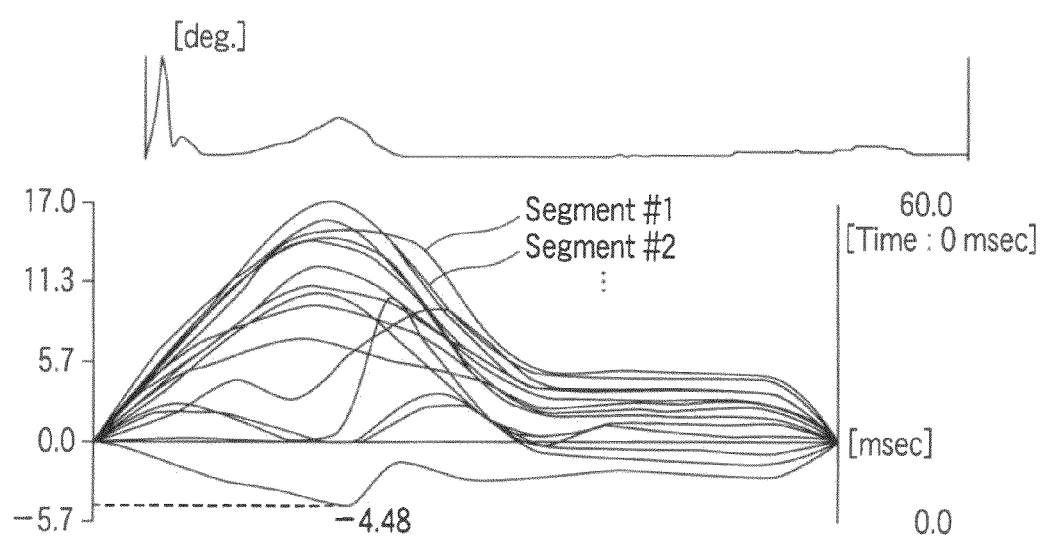
FIG. 9 is a graph showing the time curves of segment average values generated by a segment average time curve generating unit in FIG. 1.

A segment average time curve generating unit 35 generates a plurality of time curves representing temporal changes in cardiac wall motion index from a plurality of polar maps at different phases generated by the polar map generating unit 32, as shown in FIG. 9. Time curves are generated in association with the respective segments obtained by segmenting a polar map. The average of a plurality of index values in each segment is calculated. A time curve based on this average value is generated.

Figure 11:
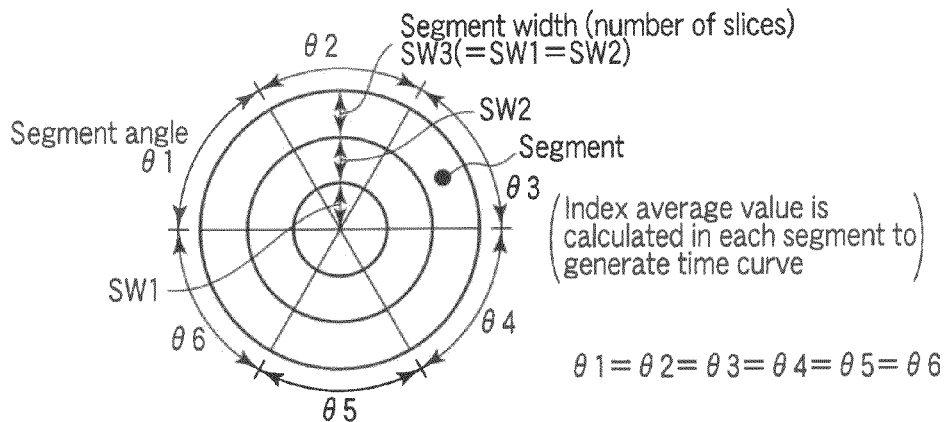
FIG. 11 is a view showing a segment set initially set by a segmentation processing unit in FIG. 1.

As shown in FIG. 11, a segmentation processing unit 34 segments a polar map template, i.e., a plurality of concentric annular areas centered on the cardiac axis, into a plurality of segments along the circumferential direction. Each annular area is segmented into six segments along the circumferential direction. The segmentation processing unit 34 initially segments the annular areas by the same width (SW1=W2=SW3) in the radial direction, and segments the respective annular areas at the same angular intervals ($\theta1=\theta2=\theta3=\theta4=\theta5=\theta6$). Upon receiving a segmentation change instruction from the operator via the input device 13, the segmentation processing unit 34 changes the angle and width of each segment based on the extracted vein position.

Figure 12:
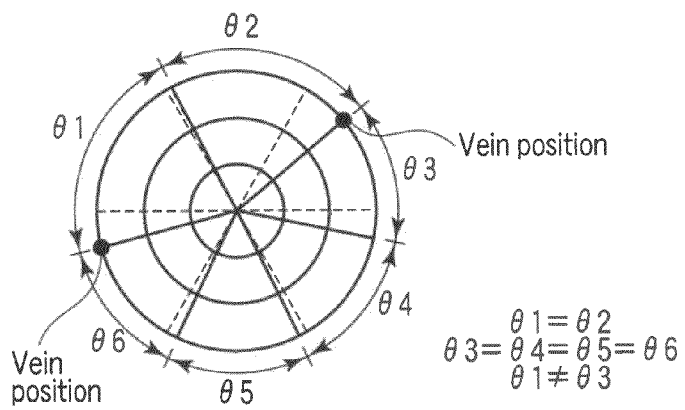
FIG. 12 is a view showing a segment set changed by the segmentation processing unit in FIG. 1 in accordance with vein positions.
Figure 13:
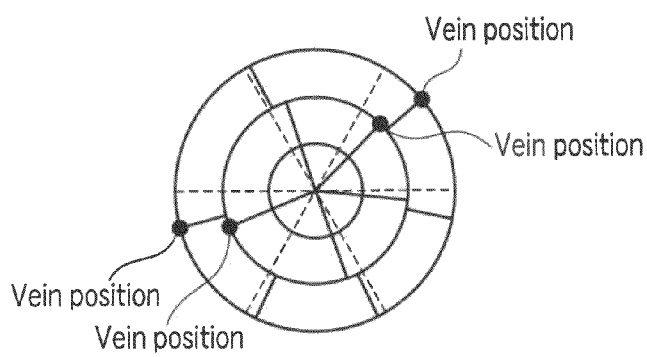
FIG. 13 is a view showing a segment adjusted for each segment by the segmentation processing unit in FIG. 1 in accordance with differences in vein position in the circumferential direction.

First of all, as shown in FIG. 12, the vein extraction unit 33 extracts, for example, two vein positions around the cardiac wall of the left ventricle on a short-axis image. The segmentation processing unit 34 changes the angle and width of each segment based on the extracted vein positions. Two segment boundary lines are set to pass through the cardiac axis and the two extracted vein positions. The angle range sandwiched between the boundary lines of the two segments is segmented into two segments at equal angular intervals ($\theta1=\theta2$). The wide angle range on the other side is segmented into four segments at equal angular intervals ($\theta3=\theta4=\theta5=\theta6$). In many cases, $\theta1 \neq \theta3'$. Note that as shown in FIG. 13, this apparatus may extract a vein area from each annular area and individually set a segment angle for each annular area in accordance with the respective vein positions.

Figure 16:
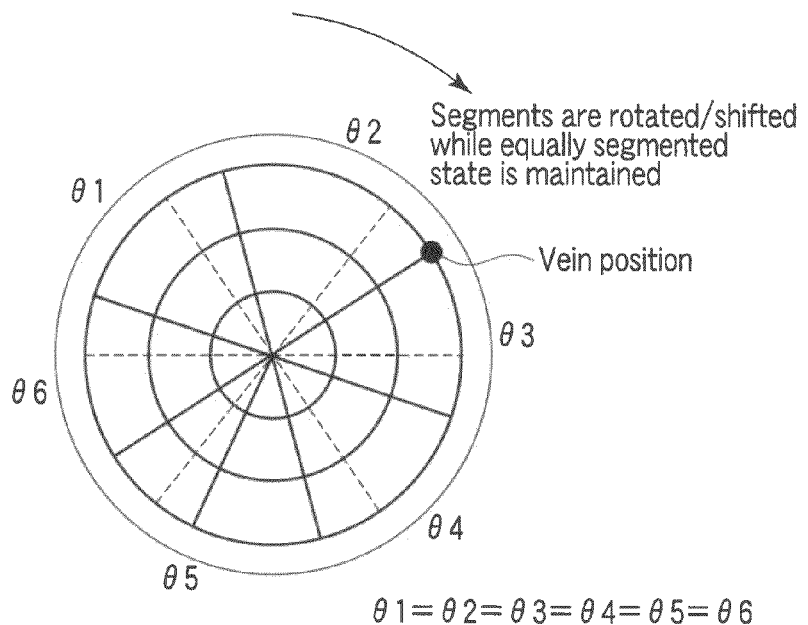
FIG. 16 is a view showing a segment set shifted by the segmentation processing unit in FIG. 1 in the circumferential direction in accordance with a vein position.

As shown in FIG. 16, the equally divided six segments may be rotated/shifted in the circumferential direction in accordance with one vein position while the equally divided state is maintained. The operator arbitrarily selects one of the segment re-setting method shown in FIG. 12 and the segment re-setting method shown in FIG. 16.

Performing segmentation in accordance with vein positions in this manner can reduce the influences of the veins on segment average values and improve the reliability of temporal changes in the average value of cardiac wall motion indices.

In addition, as shown FIG. 14, it is possible to set different segment widths SW for the respective annular areas. As shown in, for example, FIG. 15, the segmentation processing unit 34 extracts a vein central line from an ultrasonic image or a medical image obtained by another type of medical image apparatus such as a CT, calculates vectors at multiple points on the vein central line, with the apex portion being the origin of each vector, and segments an annular area at points 51 and 52 at which the angle difference between the adjacent points changes to a predetermined angle or more. This will determine the segment width SW and change the number of annular areas, as needed.

A 3D image processing unit 29 generates a two-dimensional image with a stereoscopic effect (to be referred to as a stereoscopic image) corresponding to a window on the monitor 14 from three-dimensional ultrasonic image stored in the image storage unit 28 by rendering processing including coordinate conversion, hidden line processing, and shadowing processing.

A coordinate conversion unit 36 performs coordinate conversion processing between the polar coordinate system of a polar map and the orthogonal coordinate system of short-axis images and long-axis images generated by the slice conversion processing unit 30 and stereoscopic images generated by the 3D image processing unit 29. This processing allows to identify relative positions between the orthogonal coordinate system of a short-axis image or the like and the polar coordinate system of a polar map. When, for example, the operator designates a point of interest on a polar map via the input device 13, the coordinate conversion unit 36 converts the polar coordinates of the point of interest into orthogonal coordinates on a short-axis image, and generates point mark data so as to superimpose a point mark at a position on a window corresponding to the converted orthogonal coordinates.

Figure 8:
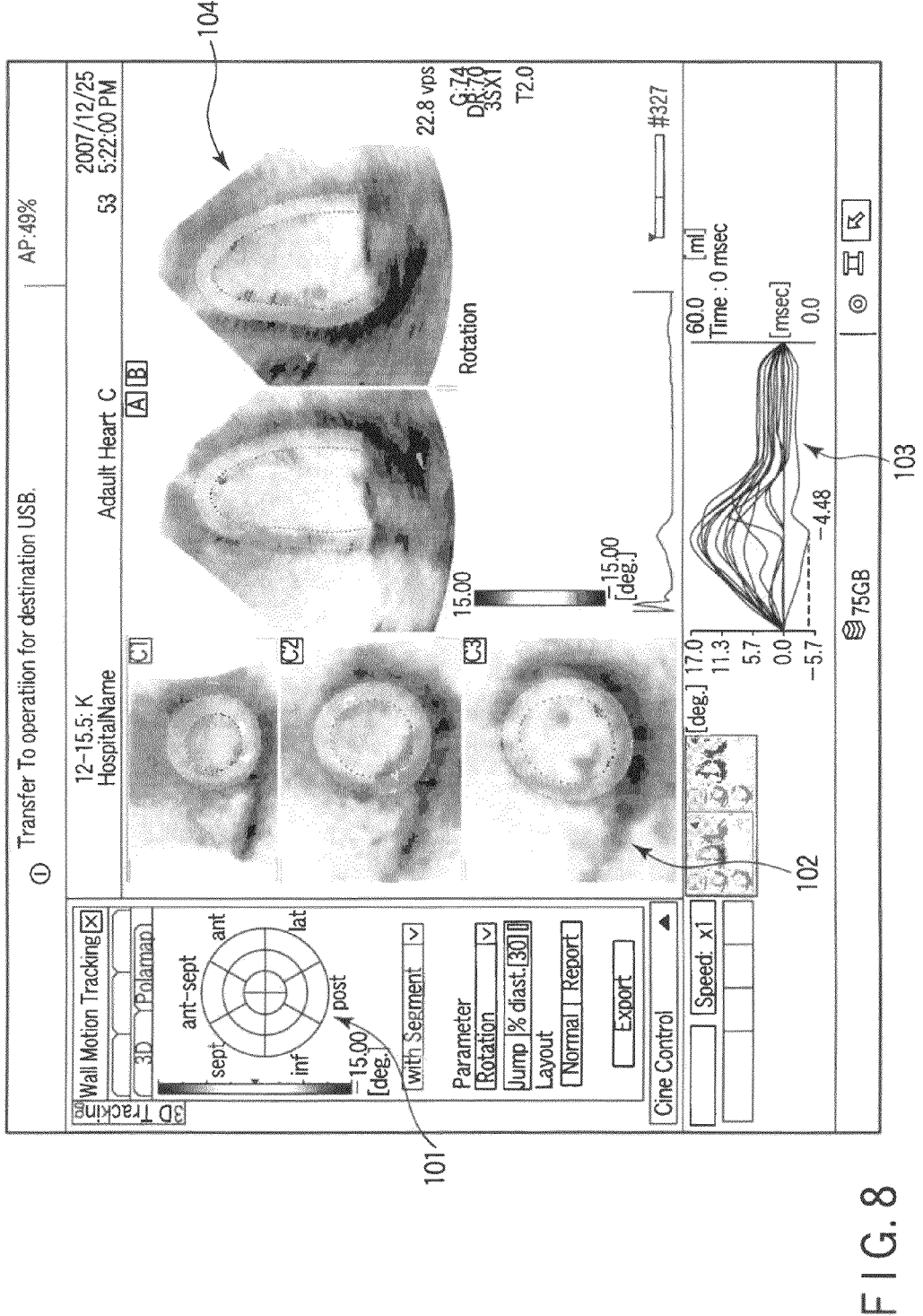
FIG. 8 is a view showing a display window example on a monitor in FIG. 1.

FIG. 8 shows a display window example on the monitor 14. The display control unit 27 forms this display window under the control of the control processor 26. The display window includes short-axis images 102 corresponding to, for example, three slices, generated by the slice conversion processing unit 30, and orthogonal long-axis images 104. A polar map 101 is also placed, together with short-axis images 102 and the long-axis images 104. In addition, a plurality of index average time curves 103 associated with a plurality of segments are superimposed and displayed on this window. Different hues are given to the index average time curves 103 to exhibit identity. Segmentation lines are superimposed on the polar map 101, and the segmentation lines are provided with the same hues as those of the corresponding time curves 103 to associate the respective segmentation lines with the time curves 103.

Figure 10:
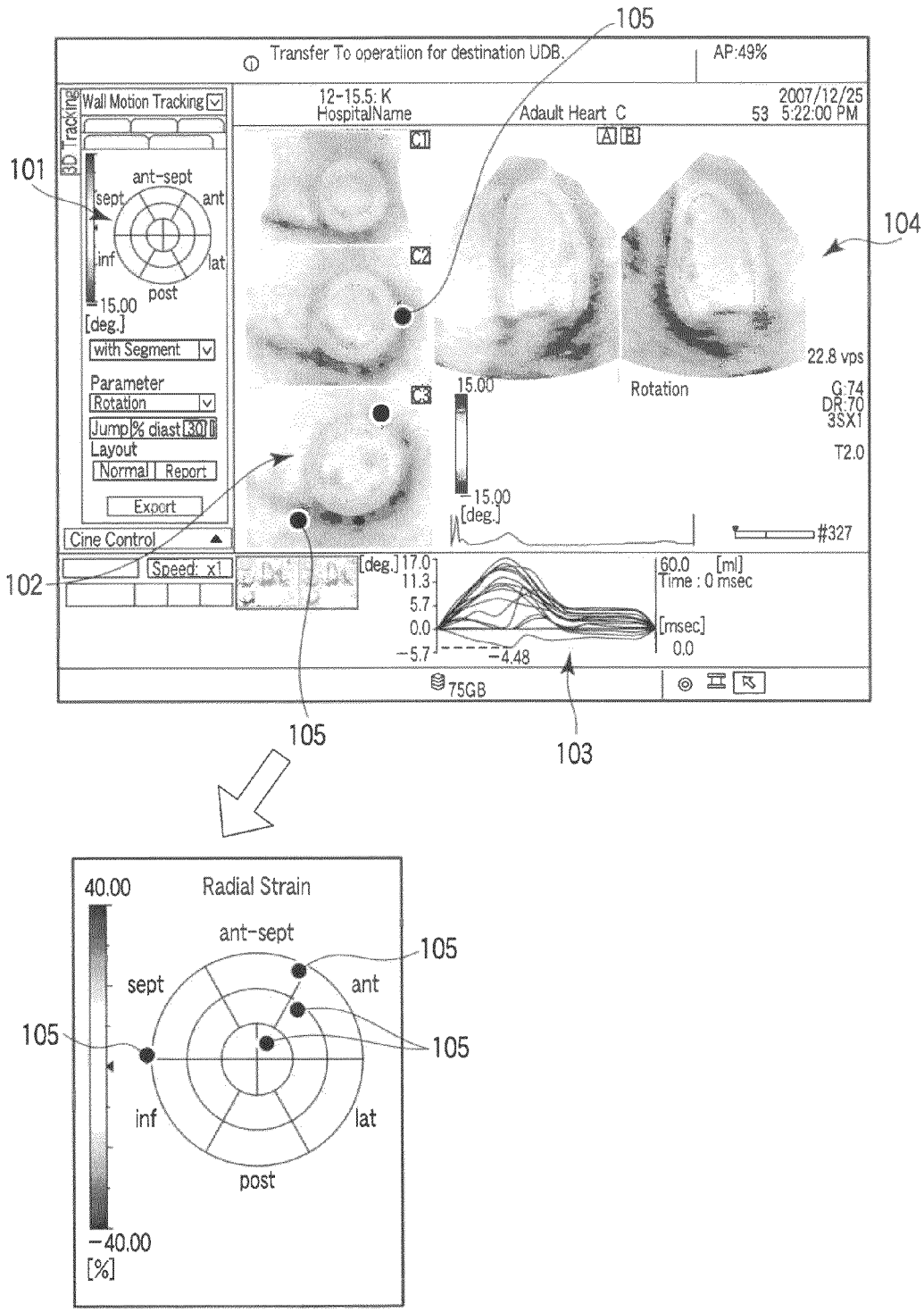
FIG. 10 is a view showing a polar map on which markers generated by a marker generating unit in FIG. 1 are superimposed.

As shown in FIG. 10, when, for example, the operator designates a point of interest on the polar map 101 via the input device 13, the coordinate conversion unit 36 converts the polar coordinates of the designated point of interest into the orthogonal coordinates of the short-axis image 102, and generates point marker data whose position is specified by the orthogonal coordinates. The display control unit 27 further converts the coordinates of the point marker data into coordinates corresponding to a display area on the short-axis image 102 on the window on the monitor 14, and superimposes a point marker 105 on the short-axis image 102.

When the operator designates a point of interest on the short-axis image 102 via the input device 13, the coordinate conversion unit 36 converts the orthogonal coordinates of the designated point of interest into polar coordinates of the polar map 101, and generates point marker data whose position is specified by the polar coordinates. The display control unit 27 further converts the coordinates of the point marker data into coordinates corresponding to a display area on the polar map 101 on the window on the monitor 14, and superimposes a point marker 105 on the polar map 101.

When the operator designates a point of interest on the long-axis image 104 via the input device 13, the coordinate conversion unit 36 converts the orthogonal coordinates of the designated point of interest into polar coordinates of the polar map 101, and generates point marker data whose position is specified by the polar coordinates. The display control unit 27 further converts the polar coordinates of the point marker data into coordinates corresponding to a display area on the polar map 101 on the window on the monitor 14, and superimposes a point marker 105 on the polar map 101. In addition, the coordinate conversion unit 36 converts the orthogonal coordinates of the designated point of interest into orthogonal coordinates of the short-axis image 102, and generates point marker data whose position is specified by the orthogonal coordinates. The display control unit 27 further converts the orthogonal coordinates of the point marker data into coordinates corresponding to a display area on the short-axis image 102 on the window on the monitor 14, and superimposes a point marker on the short-axis image 102.

In this manner, it is possible to mutually identify positions among three images, namely a polar map, short-axis image, and long-axis image.

While certain embodiments have been described, theses embodiments have been presented by way of example only, and are not intended to limit the scope of the inventions. Indeed, the novel embodiments described herein may be embodied in a variety of other forms; furthermore, various omission, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising:
    an image generating unit configured to generate data of a plurality of ultrasonic images by repeatedly scanning a three-dimensional area including a heart of an object with ultrasonic waves;
    a short-axis image generating unit configured to generate a plurality of short-axis images intersecting a long cardiac axis from the ultrasonic images;
    an index calculating unit configured to calculate indices associated with a motor function of a cardiac wall from the short-axis image;
    a polar coordinate distribution generating unit configured to generate a polar coordinate distribution of the indices;
    an average calculation unit configured to calculate average values of the indices respectively corresponding to a plurality of segments in the polar coordinate distribution;
    a display unit configured to display the polar coordinate distribution and the short-axis image;
    an operation unit configured to designate a point of interest on a vein of the displayed short-axis image; and
    a segment setting unit configured to set a boundary of the segment at a position on the polar coordinate distribution which corresponds to a position of the designated point of interest.

2. The apparatus according to claim 1, further comprising a time curve generating unit configured to generate a plurality of time curves which respectively correspond to the plurality of segments and are associated with the average values of the indices.

3. The apparatus according to claim 1, wherein the segment setting unit sets a width of the segment in a radial direction in the polar coordinate distribution in accordance with the position of the point of interest.

4. The apparatus according to claim 1, wherein the segment setting unit changes an angle of the segment in accordance with the position of the point of interest.

5. The apparatus according to claim 1, wherein the segment setting unit shifts a position of the segment in accordance with a position of the point of interest.

6. An ultrasonic diagnostic apparatus comprising:
    an image generating unit configured to generate data of a plurality of ultrasonic images by repeatedly scanning a three-dimensional area including a heart of an object with ultrasonic waves;
    a short-axis image generating unit configured to generate a plurality of short-axis images intersecting a long cardiac axis from the ultrasonic images;

an index calculating unit configured to calculate indices associated with a motor function of a cardiac wall from the short-axis image;

a polar coordinate distribution generating unit configured to generate a polar coordinate distribution of the indices;

an average calculation unit configured to calculate average values of the indices respectively corresponding to a plurality of segments obtained by segmenting the polar coordinate distribution;

a position specifying unit configured to automatically specify a vein position from the short-axis image; and a segment setting unit configured to set a boundary of the segment at a position on the polar coordinate distribution which corresponds to the specified vein position.

7. The apparatus according to claim 6, wherein the position specifying unit specifies the vein position by pattern matching using at least one vein pattern covering a local area including a vein.

8. The apparatus according to claim 6, wherein the plurality of vein patterns include a vein pattern associated with an able-bodied person and a vein pattern associated with a disable-bodied person, and one vein pattern to be applied to the pattern matching is selected from the plurality of vein patterns.

9. The apparatus according to claim 1, wherein the segment setting unit changes an angle of the segment in accordance with a position of the point of interest.

10. The apparatus according to claim 6, wherein the segment setting unit shifts a position of the segment in accordance with a position of the point of interest.

11. A medical image processing apparatus comprising:

an image storage unit configured to store data of a plurality of medical images associated with a three-dimensional area including a heart of an object;

a short-axis image generating unit configured to generate a plurality of short-axis images intersecting a long cardiac axis from the medical images;

an index calculating unit configured to calculate indices associated with a motor function of a cardiac wall from the short-axis image;

a polar coordinate distribution generating unit configured to generate a polar coordinate distribution of the indices;

an average calculation unit configured to calculate average values of the indices respectively corresponding to a plurality of segments in the polar coordinate distribution; and a segment setting unit configured to set, from the short-axis image, a boundary of the segment at a position on the polar coordinate distribution which corresponds to one of a vein position designated by an operator and a vein position specified by pattern matching.

12. The apparatus according to claim 11, further comprising a time curve generating unit configured to generate a plurality of time curves which respectively correspond to the plurality of segments and are associated with the average values of the indices.

13. The apparatus according to claim 11, wherein the segment setting unit sets a width of the segment in a radial direction in the polar coordinate distribution in accordance with the vein position.

14. The apparatus according to claim 11, wherein the segment setting unit changes an angle of the segment in accordance with the vein position.

15. The apparatus according to claim 11, wherein the segment setting unit shifts a position of the segment in accordance with the vein position.

16. The apparatus according to claim 11, which further comprises a position specifying unit configured to automatically specify a vein position from the short-axis image, and in which the position specifying unit specifies the vein position by pattern matching using at least one vein pattern covering a local area including a vein.

17. The apparatus according to claim 11, wherein the plurality of vein patterns include a vein pattern associated with an able-bodied person and a vein pattern associated with a disable-bodied person, and one vein pattern to be applied to the pattern matching is selected from the plurality of vein patterns.

* * * * *